United States Patent
Wietelmann et al.

(12)

(10) Patent No.: US 6,294,705 B1
(45) Date of Patent: Sep. 25, 2001

(54) METHOD FOR PRODUCING ALKALI METAL ALCOHOLATES

(75) Inventors: Ulrich Wietelmann, Friedrichsdorf; Uwe Lischka; Ute Emmel, both of Frankfurt am Main, all of (DE)

(73) Assignee: Chemetall GmbH, Frankfurt am Main (DE)

(*) Notice: Subject to any disclaimer, the term of this patent is extended or adjusted under 35 U.S.C. 154(b) by 0 days.

(21) Appl. No.: 09/700,210
(22) PCT Filed: May 10, 1999
(86) PCT No.: PCT/EP99/03188
  § 371 Date: Feb. 6, 2001
  § 102(e) Date: Feb. 6, 2001
(87) PCT Pub. No.: WO99/58482
  PCT Pub. Date: Nov. 18, 1999

(30) Foreign Application Priority Data

May 13, 1998 (DE) .............................. 198 21 304

(51) Int. Cl.[7] .............................. C07C 31/30; C07C 31/18
(52) U.S. Cl. .............................. 568/851; 568/852; 568/853
(58) Field of Search .............................. 568/851, 852, 568/853

(56) References Cited

U.S. PATENT DOCUMENTS 4,042,636 * 8/1977 Lenz et al. ................. 260/632 A
4,150,244 * 4/1979 Knorre et al. .................. 568/851

* cited by examiner

*Primary Examiner*—Sreeni Padmanabhan
*Assistant Examiner*—Elvis O. Price
(74) *Attorney, Agent, or Firm*—Antonelli, Terry, Stout & Kraus, LLP

(57) ABSTRACT

The invention relates to a method for producing alkali metal alcoholates by reacting alcohol with alkali metal in an aprotic, organic solvent in the presence of an H acceptor such as e.g. isoprene, butadiene, styrene or methyl styrene.

16 Claims, No Drawings

METHOD FOR PRODUCING ALKALI METAL ALCOHOLATES

This is the National Phase Application of PCT application Ser. No. EP99/03188, filed May 10, 1999.

The invention relates to a method for the preparation of alkali metal alcoholates, in which method alcohol is reacted with alkali metal in an aprotic organic solvent using a hydrogen acceptor.

Alkali metal alcoholates R-OM (R=alkyl, M=Li, Na, K, Rb, Cs) are compounds that are susceptible to hydrolysis and are often used in organic synthesis on account of their basic properties.

It is known that alkali metal alcoholates can be prepared by reacting the corresponding alcohols with an alkali metal in accordance with the reaction equation:

2R—OH+2M→2R—OM+H$_2$

R=alkyl

M=Li, Na, K, Rb, Cs

The speed of this reaction diminishes as the length of the alkyl chain increases and also as branching increases. Whilst the reaction can be successfully accelerated to a considerable extent on a laboratory scale as a result of the use of extremely finely divided alkali metal, which is produced with a particle size below 50 μm by means of high-speed stirrers, the reaction takes many hours on an industrial scale of production. Long reaction times, however, impair the economic efficiency of this alcoholate synthesis.

A method for preparing alkali metal alcoholates is known from FR-PS 1 070 601, in which alkali metal is finely distributed, in a boiling inert hydrocarbon by being stirred, and after cooling the calculated quantity of alcohol is added drop by drop to the dispersion. During the preparation of the sodium suspension, any agglomeration of the finely distributed sodium is prevented by adding a dispersive additive, such as fatty acid, surfactants or active carbon. The alkali metal alcoholate in xylene that results can be separated.

With the method known from DE-OS 34 37 152 for the catalyzed preparation of alkali metal alcoholates from alkali amalgams and alcohols, lumps of anthracite are used as the catalyst, the surface of which is preferably coated with a mixture of nickel and molybdenum oxide. Aliphatic alcohols having 1 to 4 carbon atoms are preferably used.

With the method known from DE-PS 08 45 341 for the preparation of alkali metal alcoholates that are lean in caustic alkali, amalgamated alkali metal is brought into contact with alcohol several times in the presence of catalysts, such as graphite. In this connection, it is further known from DE-PS 09 28 467 that finely distributed sodium amalgam and alcohol can be directed in counterflow with respect to a lumpy catalyst, consisting of a mixture of graphite or active carbon and metal filings.

The methods set out above have the following disadvantages:

The reaction times cannot be successfully reduced in an economical manner on an industrial scale of production by means of the use of lumpy or filing-like catalyst substances.

The necessary separation of the catalysts from the reaction product is problematic in many cases.

The use of a toxic amalgam compound as the alkali metal component is problematic on account of the impact on the workplace and environment.

Since the speed of reaction is often simply insufficient unsatisfactory when elemental alkali metal is used, in particular in the case of sterically hindered tertiary alcohols, despite the measures described, very basic organometal compounds have also been used as the alkali- metal source. This holds good in particular for the preparation of lithium alcoholates:

R—OH+R'Li→R—OLi+R'H↑

The disadvantage of this smoothly running reaction is the comparatively high price of organo-lithium compounds.

Further syntheses are based on alkali metal hydrides and amides. Whilst these reagents often react somewhat faster or clearly faster than the alkali metal in elemental form, the compounds, calculated on a molar basis, are clearly more expensive than the alkali metal. In the case of the amides, moreover, ammonia develops that has to be removed from the waste-gas stream at a cost. When hydrides are used—compared with the use of the elemental metals—twice the quantity of hydrogen develops. Whilst hydrogen is not an ecologically hazardous product, the resultant gas stream is loaded with organic compounds (solvent, alcohol) which, for ecological reasons, as far as possible should not reach the environment.

R—OH+MH→R—OM+H$_2$↑

R—OH+MNH$_2$→R—OM+NH$_3$↑

R=alkyl residue; M=alkali metal

The object of the present invention is to avoid the disadvantages in accordance with the prior art, that is, in particular to set forth a method for the preparation of alkali metal alcoholates that starts with inexpensive raw materials that are available commercially and which in a very rapid reaction supplies water-free alkali metal alcoholates whilst forming as few gaseous by-products as possible and without using solid catalysts that are difficult to separate.

The object is achieved in that the alcohol is reacted with the alkali metal (Li, Na, K, Rb, Cs) in an aprotic organic solvent, and an H-acceptor in the form of a conjugated diene or a 1-arylolefine is moreover added thereto. The reaction preferably proceeds in accordance with the following reaction scheme:

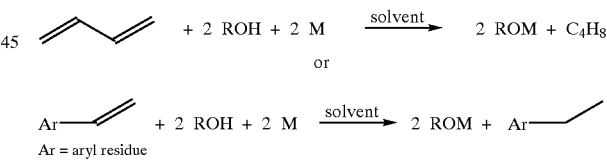

Ar = aryl residue

The presence of an H-acceptor brings about an advantageous reduction in the quantity of waste gas, from the point of view of reaction-control and environmental-protection, in comparison with the conventional reaction of alkali metal alcoholate formation.

Open-chain or cyclic, unsubstituted or substituted 1,3-dienes or unsubstituted or substituted 1-arylolefines can be used as the H-acceptors (in the case of the substituted reagents, both in the cis and in the trans form). Preferred H-acceptors for this reaction are isoprene, butadiene, cyclohexadiene-(1,3), styrene or methyl styrene.

The quantity of H-acceptor added amounts to 0.2 to 4 times, preferably 0.4 to 1.5 times, the stoichiometric quantity, that is, 0.2 to 4 mol, preferably 0.4 to 1.5 mol, relative to, in each case, 2 mol alcohol. The method can consequently even be carried out with the quantity of H-acceptor that is added lying below the stoichiometrical relationship, this increasing the economic efficiency.

In particular one of the metals Li, Na or K or mixtures of these metals can be used as the alkali metal.

It is advantageous that the alkali metal can be present in pulverulent form, granular form or lumps. In the case of Na, K, Rb or Cs in addition preferably a finely divided molten mass can be chosen. On account of its high melting point, lithium is preferably used in a solid form.

In particular in the case of the reaction of secondary or tertiary alcohols with an alkali metal, the presence of an H-acceptor results in clearly higher speeds of reaction in comparison with methods known hitherto. The reactions of i-propanol, t-butanol or t-pentanol are of particular commercial interest.

An aliphatic or aromatic hydrocarbon with 4 to 20 C-atoms or an ether or a mixture of these substances can be used as the aprotic organic solvent. The reaction can be carried out particularly well in hexane, heptane, octane, toluene, ethyl benzene, methyl-tert. butyl ether (MTBE), tetrahydrofuran (THF) or 2-methyl-THF. Commercially available hydrocarbon mixtures, such as, for example, petroleum ether, paraffin oil, high-boiling Shellsol D 70, can also be used in a particularly advantageous manner as the solvent.

The mixture of alcohol and H-acceptor is preferably added to the dispersion of alkali metal in the aprotic organic solvent. It is also possible to produce a mixture of solvent, H-acceptor and metal, to which the alcohol is added in doses. In some cases, it is also possible to add the alkali metal in a solid or liquid form to the mixture of solvent, alcohol and H-acceptor.

A solution of lithium tert-butylate in THF can be prepared in this way, for example.

The temperature of reaction is maintained at −20 to 200° C., preferably at 20 to 140° C.

The subject-matter of the invention is explained in greater detail in the following with reference to exemplifying embodiments.

EXAMPLE 1

Synthesis of Sodium Tert-butylate (STB) in Toluene in the Presence of a Stoichiometric Quantity of Styrene 4.78 g (208 mmol) Na-lumps were placed in 69.8 toluene in a 250-ml four-necked flask with a heating mantle, precision glass stirrer and reflux condenser, and heated to approximately 100° C. At the start of the addition of a mixture of 15.0 g (202 mmol) tert-butanol and 10.5 g (101 mmol) styrene, the temperature of the reaction mixture was immediately increased to 109° C. During the addition which took place in 25 minutes, no significant development of gas could be observed. Towards the end of the addition, small quantities of a white deposit could be observed on the flask wall, although this disappeared 5 minutes after the end of dosing (clear, light yellow solution). The temperature was maintained at approximately 100° C. for a further 25 minutes.

The product solution was filtered in the hot state and dried in a rotation evaporator until the weight was constant. 18.2 g (94%) STB in the form of a colourless powder was obtained.

Comparative Example A

Synthesis of Sodium Tert-butylate in Toluene Without an H-acceptor

Using the same apparatus as in Example 1, tert-butanol was dosed into a boiling Na-dispersion (containing 61.5 g sodium =2.7 mol) in toluene. After the addition of 70 g tert-butanol (35 mol %, relative to the Na-quantity that is used), 17% of the quantity of hydrogen to be expected in theory had been formed after 1.4 hours only, suggesting that the speed of reaction was substantially slower than that of Example 1 in accordance with the invention.

EXAMPLE 2

Synthesis of Lithium Tert-butylate in Tetrahydrofuran in the Presence of a Stoichiometric Quantity of Isoprene 9.62 g (1386 mmol) lithium granules (Na-content 0.43%) were placed in 400 g THF in a 1 l double-jacket reactor with a reflux condenser, drip funnel and precision glass stirrer, and a mixture of 106 g (1430 mmol) tert-butanol and 47.2 g (693 mmol) isoprene was added thereto at 15 to 35° C. The reaction started immediately at the beginning of the 45 minute dosing time; intensive cooling was necessary. After a 30 minute secondary reaction time, only a very small quantity of Li-metal was still present in an otherwise clear, slightly grey-coloured product solution. 2.35 mmol/g total base concentration (corresponding to a 95% reaction) were detected in a sample of the solution. After one further hour at 30° C., the base concentration rose to 2.43 mmol/g (corresponding to 98%). Throughout the reaction time, no significant development of hydrogen was observed.

It was possible to filter the product solution in a problem-free manner (glass frit, filtration time approximately 1 minute).

Comparative Example B

Synthesis of Lithium Tert-butylate in Tetrahydrofuran Without an H-acceptor 3.5 g (0.5 mol) Li-granules (0.77% Na-content) were suspended in 100 g THF in a 500-ml flask with a reflux condenser, drip funnel and precision glass stirrer, and a solution of 37.1 g (0.5 mol) tert-butanol in 60 ml THF was added thereto under reflux within 145 minutes. During this time, 28% of the $H_2$-quantity that was to be expected in theory was formed. After a further 3 hours boiling under reflux, a filtered sample was taken and tested for the total base (2.04 mmol/g corresponding to an 82% reaction).

After cooling, filtering was carried out by way of a glass frit. The filtration process took 100 minutes and yielded a cloudy, yellow solution. The reaction time is also longer in this comparative example than in Example 2.

EXAMPLE 3

Synthesis of Potassium Tert-amylate (PTA) in Hexane at 60° C. in the Presence of a Stoichiometric Quantity of Isoprene 25.3 g (648 mmol) of purified potassium crusts (Merck) were melted in 305 g hexane in a 0.5–1 twice clad reactor with a precision glass stirrer, reflux condenser and drip funnel, and then a mixture of 57.1 g (648 mmol) tert-amyl alcohol and 22.1 g (324 mmol) isoprene was added thereto at approximately 60° C. within 100 minutes. During the addition process, the reaction mixture became slightly cloudy, although was easy to stir. At the end of the addition, refluxing was effected for 10 minutes, with a clear, slightly yellowish solution being formed.

The filtered solution was concentrated by evaporation in a rotation evaporator under vacuum. 74.8 g (92%) of a colourless powder was obtained that had the expected composition for PTA.

EXAMPLE 4

Synthesis of Lithium Tert-butylate in THF in the Presence of a Sub-stoichiometric Quantity of Isoprene 5.2 g (0.75 mol) lithium metal granules (0.4% Na-content) were suspended in 300 ml THF in an apparatus like that in Example 3, and a mixture of 16.2 g (238 mmol) isoprene and 97.3 g (772 mmol) tert-butanol was added thereto within 3 hours. The reaction temperature was maintained at approximately 40° C. At the end of dosing, the mixture was stirred again for approximately 1 hour at 40° C.; afterwards no metallic lithium could be detected any more. The slightly cloudy solution was filtered without any difficulties by way of a glass frit (filtration time approximately 30 sec). A base concentration of 2.18 mmol/g was analyzed in the slightly grey-coloured, yet clear filtrate, this corresponding to a yield of 98%.

During the reaction phase, approximately 170 mmol $H_2$-gas had been formed, that is, approximately 45% of the metal reacted directly with the alcohol. In this Example, the quantity of isoprene used corresponded to 0.62 times the stoichiometric quantity.

What is claimed is:

1. Method for the preparation of alkali metal alcoholates by reacting alcohol with alkali metal in an aprotic organic solvent, characterised in that the synthesis is carried out in the presence of an H-acceptor, with the H-acceptor being an open-chain, unsubstituted or substituted 1,3-diene

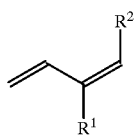

with $R_1$, $R_2$=H, alkyl, vinyl ($R_1$, $R_2$ in cis or trans position) or a cyclic 1,3-diene

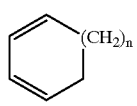

with n=1 to 5 or an unsubstituted or substituted arylolefine

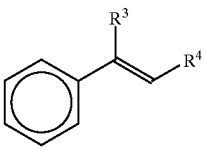

with $R_3$, $R_4$=H, alkyl ($R_3$, $R_4$ in cis or trans position).

2. Method according to claim 1, characterised in that the H-acceptor is isoprene, butadiene, cyclohexadiene-1,3; styrene or methyl styrene.

3. Method according to claim 1, characterised in that the quantity of H-acceptor used is 0.2 to 4 mol per every 2 mol alcohol.

4. Method according to claim 3, characterised in that the quantity of H-acceptor used is 0.4 to 1.5 mol per every 2 mol alcohol.

5. Method according to claim 1, characterised in that one or more of the metals Li, Na or K is or are used as the alkali metal.

6. Method according to claim 1, characterised in that the alkali metal is present in solid form (pulverulent form, granular form or in lumps) or, in the case of the Na, K, Rb or Cs, even in a finely divided, liquid form.

7. Method according to claim 1, characterised in that a secondary or tertiary alcohol is used as the alcohol.

8. Method according to claim 7, characterised in that i-propanol or t-butanol or t-pentanol is used as the alcohol.

9. Method according to claim 1, characterised in that an aliphatic or aromatic $C_4$- to $C_{20}$-hydrocarbon or an ether or a mixture of the substances mentioned is used as the aprotic solvent.

10. Method according to claim 9, characterised in that hexane or heptane or octane or toluene or ethyl benzene or methyl tert-butyl ether or diethyl ether or tetrahydrofuran or 2-methyl tetrahydrofuran is used as the aprotic solvent.

11. Method according to claim 9, characterised in that a hydrocarbon mixture, such as petroleum ether or high-boiling hydrocarbon mixtures (paraffin oil), is used as the aprotic solvent.

12. Method according to claim 1, characterised in that a mixture of alcohol and H-acceptor is added to the alkali-metal dispersion in a solvent.

13. Method according to claim 1, characterised in that the temperature of reaction is maintained at −20 to 200° C.

14. Method according to claim 13, characterised in that the reaction temperature is maintained at 20 to 140° C.

15. Method according to claim 1, characterised in that possible excess alkali metal is filtered off, and an alkali metal alcoholate solution is obtained as an end product.

16. Method according to claim 1, characterised in that at the end of the reaction possible excess alkali metal is filtered off, the reaction solution is concentrated by evaporation, and solid alkali metal alcoholate is obtained as an end product.

* * * * *